United States Patent [19]
Tomlin

[11] Patent Number: 4,738,147
[45] Date of Patent: Apr. 19, 1988

[54] LOW FLOW SAMPLING AND ANALYSIS SYSTEM

[75] Inventor: Robert L. Tomlin, Waldron, Ark.

[73] Assignee: Sampling Technology, Inc., Waldron, Ark.

[21] Appl. No.: 942,292

[22] Filed: Dec. 16, 1986

[51] Int. Cl.⁴ .............................................. G01N 1/00
[52] U.S. Cl. ..................... 73/864.81; 55/97; 55/270; 55/267; 73/863.11; 73/863.23; 73/863.31; 73/23
[58] Field of Search ................... 55/270, 97, 267; 73/863.12, 863.11, 863.23, 23, 863.31, 864.73, 864.81

[56] References Cited
U.S. PATENT DOCUMENTS

| | | | |
|---|---|---|---|
| 3,218,842 | 11/1965 | Ludwig et al. | 73/23 |
| 3,438,261 | 4/1969 | Collins, Jr. | 73/421.5 |
| 3,457,787 | 7/1969 | Maatsch et al. | 73/421.5 |
| 3,593,023 | 7/1971 | Dodson et al. | 250/43.5 |
| 3,976,450 | 8/1976 | Marcote et al. | 55/158 |
| 4,004,882 | 1/1977 | Byrne et al. | 23/254 R |
| 4,079,622 | 3/1978 | Cocola et al. | 73/863.12 |
| 4,147,500 | 4/1979 | Karlsoen | 432/2 |
| 4,191,541 | 3/1980 | Jenkins | 55/18 |
| 4,231,256 | 11/1980 | Chapman et al. | 73/863.12 |
| 4,257,258 | 3/1981 | Bovenlander | 73/23 |
| 4,485,666 | 12/1984 | Higgins et al. | 73/23 |

FOREIGN PATENT DOCUMENTS

233202  2/1986  German Democratic Rep. .... 73/23

Primary Examiner—Bernard Nozick
Attorney, Agent, or Firm—Dennison, Meserole, Pollack & Scheiner

[57] ABSTRACT

A method and apparatus are disclosed for measuring the gaseous content of industrial process gas streams. Gas is removed from the stream at a low flow rate, under 1 liter per minute, and is passed through a heated filter to remove particulates. The gas is then cooled to about 35° to 70° F. in order to condense water from the stream, and is passed through a metering pump which supplies a precisely metered amount of gas which can be mixed with air for dilution. The gas is then analyzed for the desired components.

16 Claims, 2 Drawing Sheets

LOW FLOW SAMPLING AND ANALYSIS SYSTEM

BACKGROUND OF THE INVENTION

This invention relates to a process and apparatus for measuring the gaseous content of industrial process gas streams, in which a portion of a process gas stream is extracted, conditioned for analysis, and transported to a gas analysis system.

Many industrial processes can benefit from the continuous measurement of process gas streams before and after the process stream gas and/or particulate scrubbing systems. Due to the extreme environment of the process gas stream, before and after many process scrubbers, no gas analysis system to date has demonstrated reliable continuous operation in both of these environments.

Many gas analysis systems are not specific to one gas. Gases other than the gas or gases of interest may cause an erroneous response in the analysis system. Dilution of the process gas stream with air to achieve lower concentrations of the interfering gases has been demonstrated as a reliable way to eliminate many interference problems. In process streams with constant and known composition, dilution of the process stream with conventional flow controllers, such as needle valves, fixed orifice, or automatic compensation needle valves, has given reliable and accurate gas dilutions. However, in process streams with widely varying compositions, all conventional flow controllers demonstrate inaccuracies in flow due to the changing viscosity of the gases in the process gas stream. A method was needed to allow accurate and interference free measurement of process gas streams with widely varying gas compositions.

Filtering the process gas stream for particulate matter, water, acids, and other compounds that interfere with gas analysis has always been a serious problem for industry. To achieve the analytical response time required for process control and EPA mandated response time requirements, relatively high flow rates (1 to 80 liters per minute) were extracted from the process. The higher the flow rate extracted from the process, the larger the problem becomes for sample gas conditioning. A method was needed that extracts a very low volume of gas from the process, yet still allows the higher flow rates required for fast response time.

Due to trends in the EPA regulations to apply to smaller industries, and the needs of these smaller industries to achieve tighter process controls, a lower cost method of monitoring these processes needed to be developed. Current state-of-the-art continuous process gas analytical systems are very complex and require extensive training of maintenance and operation personnel to adequately maintain these systems. A gas sampling and analysis system was needed of greatly reduced complexity, while maintaining a higher level of reliability and accuracy.

SUMMARY OF THE INVENTION

It is an object of the present invention to provide a gas sampling and analysis system which allows accurate and interference free measurement of process gas streams with widely varying gas compositions.

It is another object of the present invention to provide a gas sampling and analysis system which extracts a very low volume of gas from the process, yet still allows high flow rates required for fast response time.

It is a further object of the present invention to provide a gas sampling and analysis system of greatly reduced complexity, which maintains a high level of reliability and accuracy.

These and other objects are attained according to the present invention which provides an apparatus and method for gas sampling and analysis from a process gas stream, the process including the steps of:

(a) extracting a gas sample from the stream at the rate of less than about 1 liter per minute;

(b) filtering the gas sample through a heated filter;

(c) reducing the temperature of the filtered sample to condense water from the sample;

(d) drawing predetermined quantities of the filtered, reduced temperature sample through a metering pump, and mixing the pump sample, if necessary, with a predetermined quantity of gaseous diluent; and (e) passing the diluted sample to an analysis device.

DETAILED DESCRIPTION OF THE INVENTION

Figure 1:
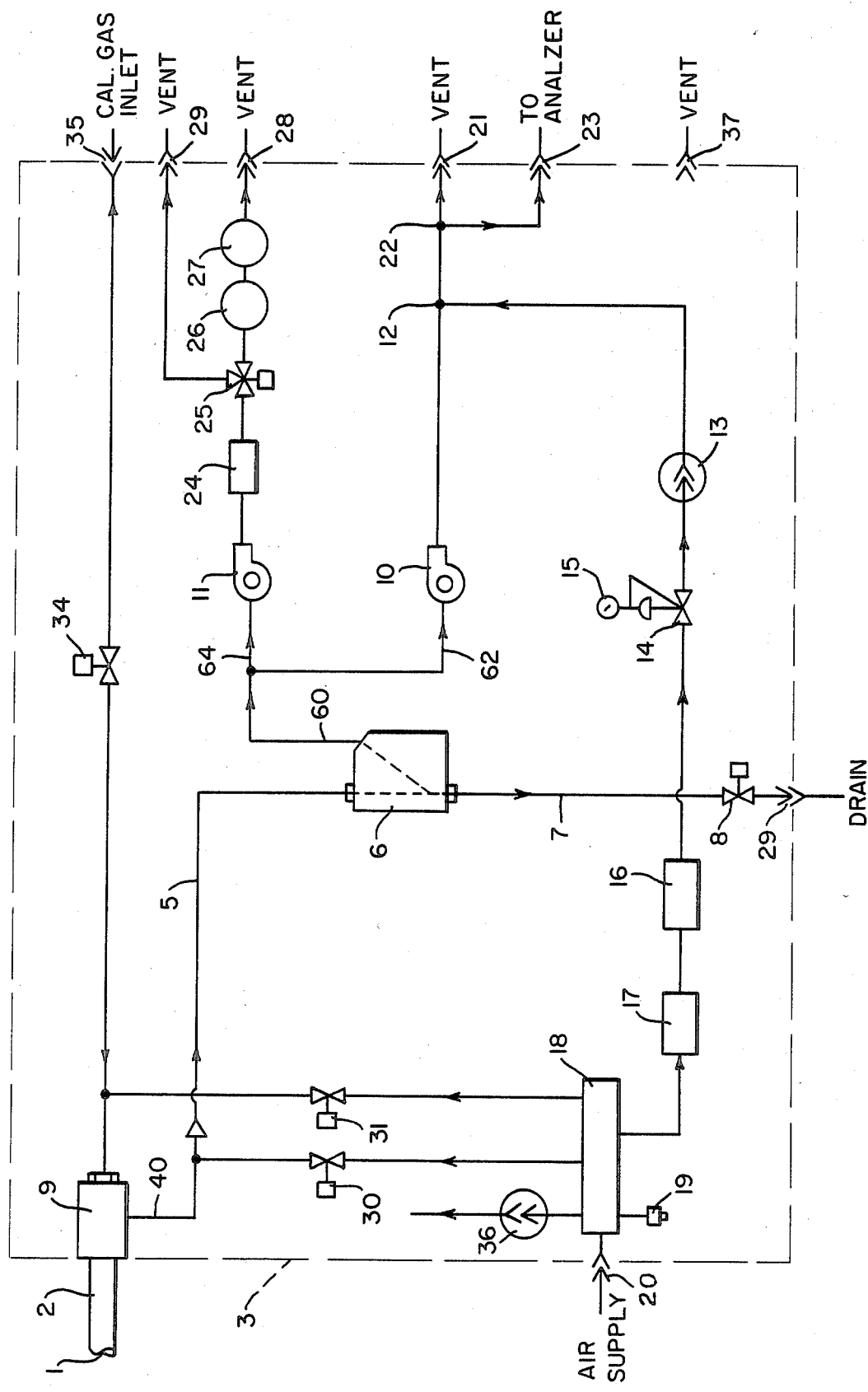
FIG. 1 is a schematic diagram of a gas sampling and analysis system according to the invention.

The low flow sampling and analysis system has been developed to solve many of the existing problems with present sampling systems. A low flow probe solves the problem of sampling before and after process scrubbers by extracting a very small sample of the process stream. The flow rate of the extracted sample, less than 1 liter/min, and preferably 10–200 cc/min, allows a large reduction in the size and complexity of the sample conditioning system. Due to the low extracted flow rate, no filters are required in the sampling probe, and due to the low sample velocity in the sampling probe, a large fraction of the process particulate matter settles out on the probe walls and is easily removed by a periodic probe blowback with air or steam. The sampling probe is typically a section of pipe of approximately ½ inch O.D. and ⅜ inch I.D. formed of a material selected for compatibility with the process stream. Suggested materials for the probe include 316 stainless steel, Hastelloy C-276, ceramic and Hastelloy C-276 with a Teflon liner. However, any material that is found compatible with the process stream and shown not to react with the gas or gases to be measured may be used.

Response time requirements have been met with the low flow sampling and analysis system by diluting the extracted gas from the probe immediately after conditioning. The low flow rate from the probe can be diluted with any air flow required to meet response time and sensitivity requirements of a remote analysis system. Typical flow rates to an external analysis system are in the range of 5 to 10 liters per minute, and give analytical instrument response times of 30 seconds to 3 minutes, depending upon application. This response time is adequate for most process control and environmental monitoring requirements. Dilution of the process stream immediately at the sample source, with dry instrument air (−40 degrees F. dewpoint), allows a further simplification of the gas conditioning system. Permeation dryers and heated sample lines are not required. Moreover, the dewpoint of the gas stream leaving the low flow sampling and analysis system is largely a function of the dewpoint of the dilution air, due to the high dilution ratio of the process gas to dilution air flow rates. Dilution ratios of 50:1 to 100:1 are easily achieved, and yield exit sample dewpoints of −25 to −35 degrees F. which allow use of unheated sample lines in all but the most extreme of environments.

Obtaining precise flow rates from process streams of varying gas composition is accomplished by using a positive displacement metering pump. Precise flow control is achieved by controlling the inlet and outlet pressure of the metering pump to essentially atmospheric conditions. The outlet of the pump is vented to atmospheric pressure. The inlet of the pump is connected to the process through the sampling probe. Most process stacks or ducts are operated at essentially atmospheric pressure conditions ($\pm 5''H_2O$). For process streams or ducts that operate at pressures greater than $\pm 5''H_2O$, a small portion of the process is vented to atmospheric pressure and a sample is drawn from this vent. This method of extracting a sample from a process stream allows the precise flow control required for accurate dilution of the process stream to lower concentrations and is not affected by the viscosity of the gases of the process stream.

The operation of the gas sampling and analysis system of the invention will now be discussed with reference to the system shown in the drawing figures.

All components for the low flow sampling and analysis system are enclosed within a 24 inch (H.) X 24 inch (W.) X 8 inch (D.) fiberglass enclosure 3, which is designed to be installed at the process sampling point on a standard four inch 150 pound pipe flange 44. A sampling probe 2 is inserted through the pipe flange and extends into the process stream, although for those process applications that require analytical system installation remote from the process, a process vent gas stream may be piped to the enclosure location. Instrument air and power are provided by the user at the installation site.

1. Normal Sampling Mode

Process gas enters the low flow sampling and analysis system at the probe tip 1. The process gas moves down the probe 2 at a low flow rate (10–200 cc/min.). Much of the larger particulate matter drops out on the probe walls due to the extremely low sample velocity. From the sampling probe, the process gas enters the temperature controlled analysis system enclosure 3. The interior of the enclosure is controlled to a predetermined temperature above the expected ambient temperature, for example $45 \pm 3$ degrees C., by an electronic temperature controller, silicone strip heaters, and an enclosure air stirring fan, not shown.

Figure 2:
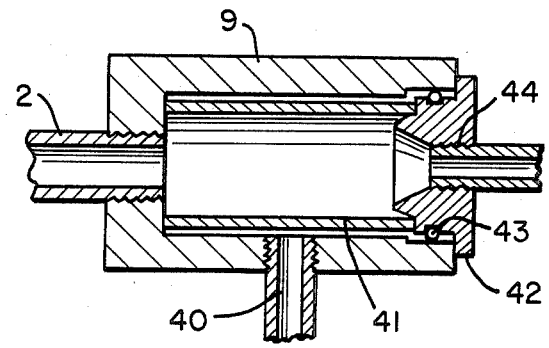
FIG. 2 is a sectional view of a heated filter used in the sampling and analysis system.

The enclosure is temperature controlled to provide improved stability for the flow control components within the enclosure. From probe 2, the process gas enters heated filter 9, shown in cross-section in FIG. 2. Heated filter 9, temperature controlled at 230 degrees F., is heated by two cartridge heater elements and controlled by a bi-metal thermostat, and is provided to accomplish final filtering of the extracted process gas. Contained within heated filter 9 is a glass fiber filter element 41. This filter element filters the process gas to less than 0.1 micron. The filter element can be replaced by removing filter cap 42, which is sealed with O-ring 43. A port 44 in filter cap 42 is provided to introduce calibration gas into the filter and to provide a port for introduction of blowback air. The sample gas is extracted from heated filter 9 through port 40.

Figure 3:
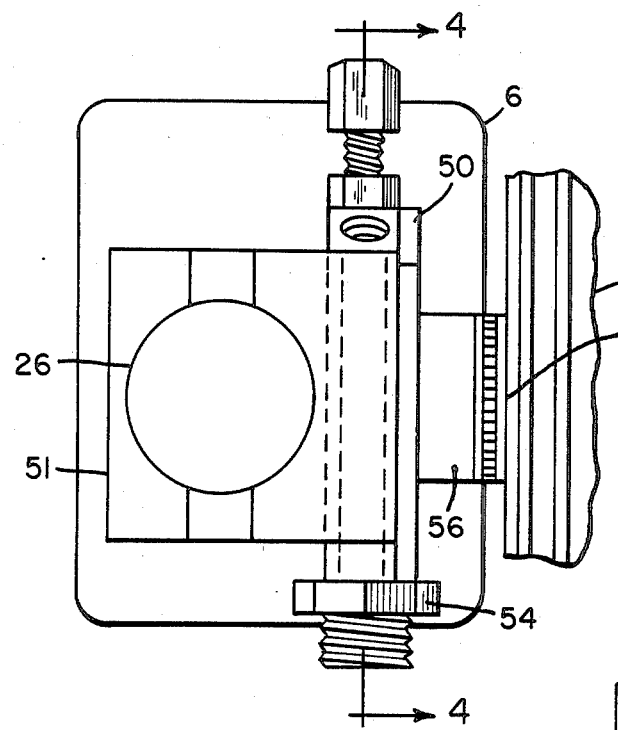
FIG. 3 is a front view of a heat exchanger enclosure of the sampling and analysis system.
Figure 4:
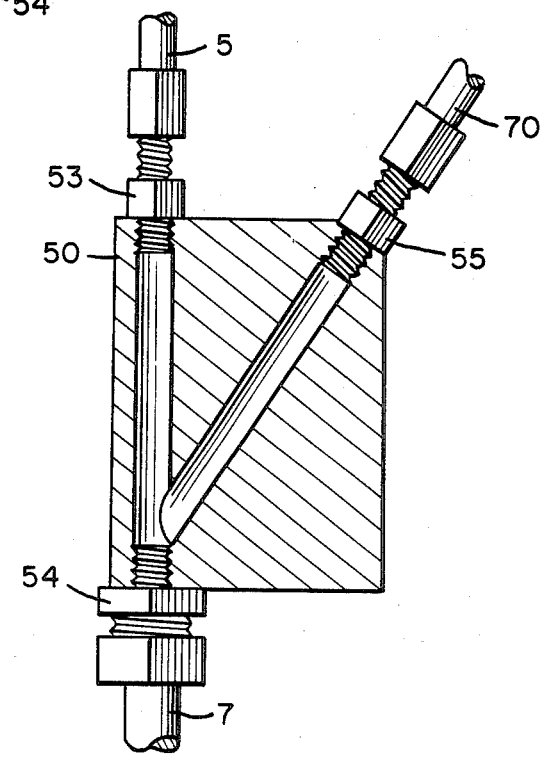
FIG. 4 is a cross-sectional view of a heat exchanger of the sampling and analysis system, along line 4—4 of FIG. 3.

From port 40, the process gas enters a Teflon sample line 5 and is close connected to the thermoelectrically cooled heat exchanger 6, shown in detail in FIGS. 3 and 4. The heat exchanger body 50 is constructed of Teflon (polytetrafluoroethylene) and is contained within an aluminum block 51. The aluminum block, and thus the Teflon exchanger, is cooled by thermoelectric cooler 52 and thermoelectric cooler power supply 63.

The heat exchanger includes a gas inlet port 53 connected to Teflon sample line 5, liquid outlet port 54 and gas outlet port 55. Thermoelectric cooler 52 transfers heat from the aluminum exchanger block 51 through an aluminum transfer plate 56. Heat removed from the heat exchanger block 51 is transferred outside the enclosure 3 to heat sink 57. Heat sink 57 is located outside the heat exchanger and is provided with a fan, not shown, for forced air cooling.

The temperature of the exchanger is controlled by controlling the power to the thermoelectric cooler with a bi-metal thermostat. By selecting a thermostat with a different temperature set point, exchanger temperatures between 35° and 70° F. may be selected for different process applications. For many process applications, 40° F. is the preferred exchanger temperature. The low flow rates used in the sampling system allow for a smaller and highly efficient heat exchanger design. The sample gas leaving the exchanger at port 55 has a dewpoint of approximately the selected exchanger temperature.

The condensate from the exchanger, containing water, acids and any particulate trapped by the condensing liquid droplets, drains from port 54 into a section of tubing 7 leading to a drain valve 8. Due to the low flow rates involved, the tubing can act as a reservoir for the collected liquids. Sample loss within the exchanger is minimal, due to the straight pass design of the exchanger and the low pH of the collected condensate.

From the gas outlet 55 of heat exchanger 6, the gas line 60 splits into two parallel flow paths 62 and 64. One path 62 is directed to a precision piston metering pump 10. Due to the precise temperature control of the enclosure and the relative stability of the inlet and outlet pressures of the pump, an extremely stable flow rate, free of gas viscosity related flow errors, is established.

A metering pump can be obtained with all ceramic construction or various combinations of ceramic, carbon and stainless steel construction, to meet various process compatibility needs. A suitable pump is sold by Fluid Metering, Inc. under the designation RP-G400-1CKY. From the outlet of metering pump 10, the conditioned process gas flows to mixing junction 12. At mixing junction 12, a diluent gas, i.e. dilution air from flow orifice 13 can be mixed with the precise and known flow from metering pump 10.

The flow rate from metering pump 10 can be varied from 0 to 100 cc/min. by adjusting the piston stroke length. The dilution air flow rate can be adjusted by changing the orifice diameter 13. These flow rates can be easily determined from the concentration range of the gas analysis system and expected concentration of the gas to be analyzed in the process stream.

The dilution air source and flow control components consist of a precision pressure regulator 14, pressure gauge 15, a 0.1 micron particulate filter 16, a chemical scrubber 17, an air distribution manifold 18, a dilution air low pressure alarm switch 19, and a dilution air inlet 20. The chemical scrubber 17 removes impurities from the dilution air such as $SO_x$ and $NO_x$, that may cause a false response in the gas analysis system. The combination of a precise and stable flow rate from the metering pump 10, and a precise and stable flow rate from the air dilution orifice 13, allows a precise and stable gas dilution to occur at mixing junction 12.

From mixing junction 12, the diluted and mixed process gas flows to atmospheric vent 21. At point 22 on the vent line, an extraction port is established, to remove a fraction (not more than 90%) of the diluted gas stream for transport to a remote gas analysis system. The gas flow for remote analysis exits the enclosure at 23. The process gas is transported from exit bulkhead 23 to the remote gas analysis system by an external sampling pump, not shown. The heated enclosure 3 is air purged with air through purge orifice 36 and enclosure vent 37, in order to prevent external dust and corrosive gases from contaminating the internal electronic and flow components. The flow rate of purge orifice 36 is approximately 5 liters/min.

2. Oxygen and Carbon Monoxide Measurement

From heat exchanger 6, a second gas stream 64 is provided for direct measurement of carbon monoxide and oxygen. This stream 64 is transported by metering pump 11 to a chemical scrubber 24, sample hold valve 25, oxygen measurement cell 26, carbon monoxide measurement cell 27, and then to an atmospheric vent at bulkhead 28. This second flow path is provided by metering pump 11 to provide for analysis of those gases where dilution of the process gas is not required or is undesirable. Metering pump 11 is a diaphragm type variable flow pump such as the Spectrex AS121-3. The flow rate of pump 11 is normally adjusted to between 50 and 100 cc/min. Other flow rates are obviously possible and desirable in certain applications. Due to the nature of the oxygen and carbon monoxide measurement cells, normally of the electrochemical type, precise flow control is not required; the $O_2$ and CO measurement cells are not flow sensitive.

It is possible to extend the life of the $O_2$ measurement cell by reducing the temperature at which it operates. According to an embodiment of the invention shown in FIG. 3, $O_2$ cell 26 is located in heat exchanger block 51 in order to provide operation at a constant, reduced temperature. The constant temperature provided by enclosing $O_2$ cell 26 within exchanger block 51 also improves the stability of the $O_2$ cell output.

From metering pump 11, the undiluted process gas flows to chemical scrubber 24. Chemical scrubber 24 is provided to remove those compounds that affect the life or accuracy of measurement cells 26 and 27. Normally the scrubber is filled with an alumina substrate coated with potassium permanganate, which removes sulfur and nitrogen compounds. From chemical scrubber 24, the undiluted process gas flows to the sample hold valve 25. The sample hold valve 25 is used to stop the flow of process gas to the $O_2$ and CO measurement cells during the blowback and purge modes of operation. When the sample hold valve 25 is energized, process gas flow is diverted to vent bulkhead 29. The $O_2$ and CO cells have sufficient internal volume such that stopping the flow to the cells causes the cell outputs to remain at a constant level until sample hold valve 25 is deenergized.

The sample hold valve 25 is energized for 3 to 5 minutes after a purge mode. Holding the output signals of the cells constant during the blowback and purge mode, allows the $O_2$ and CO signals to be useful for process control applications where interruption of the output signal would cause a loss of control of the controlled process. From the sample hold valve 25, the gas flows through the oxygen cell 26, the carbon monoxide cell 27, and then to an atmospheric vent at enclosure bulkhead 29.

Typical $O_2$ and CO analysis cells are sold by Teledyne, Inc. under the designation A5 and 26021, respectively.

3. Blowback and Purge Mode

The blowback and purge mode of operation is used to remove any accumulated deposit of particulate from the sample probe 2, the sample line 5, the heat exchanger 6, and the heated filter 9. The blowback and purge mode is also used to drain any collected condensate from the heat exchanger 6, through reservoir tubing 7 and drain valve 8.

Blowback valves 30 and 31 connect the air supply, respectively, to sample line 5, and the outlet of the heated filter 9. Purge valve 8 is connected in line 7 and drains the condensate from heat exchanger 6.

Blowback and purge valves 30, 31 and 8 are energized for 5 to 10 seconds and then return to their normally deenergized state. The blowback and purge mode is initiated at 15 to 60 minute intervals depending upon application. The sample hold valve 25 is energized at the same time that the blowback and purge mode is initiated and remains on for 3 to 5 minutes after the blowback and purge mode has ended. Control of the blowback/purge valves 30 and 31, the drain valve 8 and the sample hold valve 25 is accomplished either by internal electronic timers, for stand-alone systems, or by a remote controller for those applications that have a computer system or a programmable controller as a part of the application.

Blowback/purge valve 30 is used to remove accumulated particulate from sample line 5, heated filter element 41, and the heat exchanger 6. The positive pressure created in the heat exchanger 6 and the reservoir line 7 also aids in draining any accumulated condensate.

Blowback valve 31 is used to remove any accumulated deposit in the heated filter 9 and the sample probe 2.

Drain valve 8, which is used to drain the accumulated condensate from reservoir tubing 7, is a specially constructed plastic valve designed to handle extremely acidic or basic liquids and slurries. A suitable valve, made of Noryl plastic, is available from Skinner under the designation V42LAOJV022.

4. Calibration Mode

Calibration of the low flow sampling and gas analysis system is accomplished by introducing a calibation standard gas at the calibration gas inlet port 35 through calibration valve 34 and into the interior of the heated filter 9. The calibration gas flow rate is set externally to be greater than 1.5 times the process gas flow pulled by metering pumps 10 and 11. This method of calibration causes a calibration standard gas to be drawn through all of the active components of the sampling and conditioning system. Any gas loss due to contamination of sampling system components, leaks, or flow instability of flow controlling components, may be detected and/or corrected for by observation of the calibration response. Excess calibration gas flow over and above that pulled by metering pumps 10 and 11 is vented through the sampling probe 2 and into the process stream. A calibration gas standard is introduced at calibration gas inlet bulkhead 35, in turn, for each gas component being measured.

The sampling and analysis system of the invention finds application in a number of industries where precise measurement of gaseous content is required. The following is a partial list of applications for this system:

PULP AND PAPER INDUSTRY

1. Recovery Boiler
   a. Before precipitator —$O_2$, CO, total reduced sulfur, $SO_2$, $NO_x$
   b. After Scrubber —$O_2$, total reduced sulfur, $SO_2$, $NO_x$.
2. Lime Kiln
   a. Before Scrubber —$O_2$, combustibles, CO
   b. After Scrubber —$O_2$, total reduced sulfur.

UTILITIES

1. Before Scruber —$O_2$, CO, $SO_2$, $NO_x$
2. After Scrubber —$O_2$, $SO_2$, $NO_x$.

PETROCHEMICAL

1. Natural Gas Production
   a. Sulfur Recovery Units —$O_2$, $SO_2$.
2. Fluid Catalytic Cracking Units
   a. $O_2$, $SO_2$.

CEMENT INDUSTRY

1. Before Scrubber —$O_2$, CO, $SO_2$, $NO_x$, combustibles
2. After Scrubber —$O_2$, $SO_2$, $NO_x$.

INDUSTRIAL BOILERS

1. Before Scrubber —$O_2$, CO, $SO_2$, $NO_x$, combustibles.
2. After Scrubber —$O_2$, $SO_2$, $NO_x$.

In the above applications, "total reduced sulfur" refers to sulfur-containing gases which do not contain oxygen, for example hydrogen sulfide, dimethyl sulfide, methyl mercaptan, etc. The term "combustibles" refers generally to any gases which will burn, and more particularly to hydrocarbons.

EXAMPLE

The low flow sampling and analysis system of the invention is used to sample and analyze stack gases from the recovery boiler in a kraft pulp mill. The stack gases to be measured are total reduced sulfur-containing gases (TRS) at an average concentration of 5 ppm, oxygen at an average concentration of 4% and carbon monoxide at an average concentration of 300 ppm.

The probe is placed at the outlet of the precipitator and samples stack gases at a temperature of about 700° F. For this application, Hastelloy C-276 probe was selected, and because the stack temperature is above 300° F., a Teflon liner is not required. The stack diameter is 8 feet, and the probe length is selected to place the probe tip slightly greater than 3 feet (approximately 1 meter) from the stack wall.

At the sampling location, the ambient temperature varies between −10° F. and 105° F. Accordingly, the enclosure temperature is set to 113° F. (45° C.) to insure a constant enclosure temperature slightly higher than the highest expected ambient temperature.

A remote TRS analyzer is utilized having a full scale range of 0.5 ppm. Since measurement of actual TRS concentrations up to 30 ppm is desired, dilution with air at a ration of 60:1 is necessary. Metering pump 10 is adjusted for a flow rate of 83 cc/min, and dilution orifice 13 is opened to permit an air flow of 5 liters/min. At this dilution, a full scale TRS analyzer response will be obtained when the concentration of TRS in the stack gases is 30 ppm. Exact calibration of the TRS analyzer is accomplished in a normal manner, utilizing zero and span potentiometers located on the analyzer.

Metering pump 11 is adjusted for a flow rate of 100 cc/min. This flow rate is selected to provide a 95% analyzer response to a step change in the inlet concentration in less than 2 minutes. Oxygen and carbon monoxide analyzers are selected so that no dilution of the gas is required.

The total stack gas sampled through the probe by the device is about 200 cc/min.

In order to calibrate the analyzers, calibration gases are injected in turn at port 35 with valve 34 energized, and the zero and span response of each analyzer is adjusted to agree with the known calibration gas. The calibration routine is usually automated utilizing an external controller.

Calibration gases are selected to give an 80% of full scale response for each analyzer. Thus, the TRS analyzer is calibrated with 24 ppm $H_2S$ in a nitrogen balance, and zero is set with zero grade air. The oxygen analyzer is calibrated with zero grade air containing 20.9% oxygen and zero is set with zero grade nitrogen. The CO analyzer is calibrated with 800 ppm carbon monoxide in a nitrogen balance, and zero is set with zero grade air.

What is claimed is:

1. A method for sampling and analysis of a process gas stream of variable composition and viscosity, comprising the treating steps of:
   (a) extracting a gas sample from said stream at the rate of less than about 1 liter per minute;
   (b) filtering said gas sample through a heated filter;
   (c) reducing the temperature of said filtered sample to condense water from the sample, and separating said condensed water;
   (d) drawing predetermined quantities of said filtered, reduced temperature sample through a metering pump;
   (e) mixing said pump sample with a predetermined quantity of gaseous diluent; and
   (f) passing said pump sample and diluent to an analysis device, wherein said gas sample is maintained substantially at atmospheric pressure throughout said treating steps.

2. A method according to claim 1, wherein said gas is sampled at a rate of 10–200 cc/min.

3. A method according to claim 1, wherein said sample gas is diluted with dry air having a dewpoint of about −40° F.

4. A method according to claim 1, wherein said pump sample is diluted with dry air at an air to gas ratio of between about 50:1 and 100:1.

5. A method according to claim 1, wherein said sample is reduced in temperature to about 35° to 70° F. to condense water.

6. A method according to claim 5, wherein said sample is reduced in temperature to about 40° F.

7. A method for sampling and analysis of a process gas stream of variable composition and viscosity, comprising the treating steps of:
   (a) extracting a gas sample from said stream at the rate of less than about 1 liter per minute;
   (b) filtering said gas sample through a heated filter;

(c) reducing the temperature of said filtered sample to condense water from the sample, and separating said condensed water;

(d) drawing predetermined quantities of said filtered, reduced temperature sample through a metering pump;

(e) passing said pump sample to an analysis device; and (f) providing a second metering pump in parallel with said metering pump, drawing a quantity of said filtered, reduced temperature sample through said second metering pump, and passing the output of said second metering pump directly to additional gas analysis means, wherein said gas sample is maintained substantially at atmospheric pressure throughout said treating steps.

8. A method according to claim 7, wherein said gas is sampled at a rate of 10–200 cc/minute.

9. A method according to claim 7, wherein said sample gas is diluted with dry air having a dew point of about −40° F.

10. A method according to claim 7, wherein said pump sample is mixed with a predetermined quantity of gaseous diluent before said step of passing.

11. A method according to claim 10, wherein said pump sample is diluted with dry air at an air to gas ratio of between about 50:1 and 100:1.

12. Apparatus for sampling and analysis of a process gas stream of variable composition and viscosity, comprising:

(a) means for extracting a gas sample from the stream at a rate of less than about 1 liter per minute;

(b) heated filter means for removing particulate matter from the extracted gas sample;

(c) heat exchanger means for reducing the temperature of the filtered gas sample to condense water therefrom, and for separating condensed water from the sample;

(d) precision piston metering pump means connected to an output of said heat exchanger means for supplying a predetermined quantity of the reduced temperature gas;

(e) means for providing a diluent gas for combination with the predetermined quantity of reduced temperature gas;

(f) means for passing a combination of diluent gas and reduced temperature gas to an analysis device, and (g) means for maintaining the gas sample substantially at atmospheric pressure within said apparatus.

13. The apparatus according to claim 12, wherein said heat exchanger means comprises a polytetrafluoroethylene body having passages for flow of gas, an aluminum block in which said polytetrafluoroethylene body is located, and a thermoelectric cooler in conjunction with and for reducing the temperature of said aluminum block.

14. The apparatus according to claim 12, additionally comprising a second pump means connected to said output of said heat exchanger means in parallel with said precision piston metering pump means, and at least one additional gas analysis device connected to the output of said second pump means.

15. The apparatus according to claim 12, operable in a sampling mode and a purge mode, wherein said source of dilution air is selectively connected to said heated filter and between said heated filter and said heat exchanger means to remove particulate in the purge mode.

16. The apparatus according to claim 15, additionally comprising a second pump means connected to said output of said heat exchanger means in parallel with said precision piston metering pump means, at least one additional gas analysis device connected to the output of said second pump means, and a three way valve interposed between said second pump means and said at least one additional gas analysis device, said valve venting gas to the atmosphere during and after a purge mode, and passing gas to said at least one additional gas analysis device in the sampling mode.

* * * * *